United States Patent [19]  
Bowers

[11] Patent Number: 4,656,189  
[45] Date of Patent: Apr. 7, 1987

[54] ANTI-JUVENILE HORMONES

[75] Inventor: William S. Bowers, Geneva, N.Y.

[73] Assignee: Cornell Research Foundation, Inc., Ithaca, N.Y.

[21] Appl. No.: 739,886

[22] Filed: Nov. 8, 1976

Related U.S. Application Data

[63] Continuation-in-part of Ser. No. 613,991, Sep. 17, 1975, abandoned.

[51] Int. Cl.$^4$ .................... A01N 43/16; C07D 309/22
[52] U.S. Cl. .................................... 514/456; 514/452; 549/408
[58] Field of Search .................... 424/283, DIG. 12; 260/345.7; 514/456; 549/408

[56] References Cited

U.S. PATENT DOCUMENTS 3,725,551  4/1973  Bowers .................... 424/DIG. 12
3,957,763  5/1976  Chodnekar et al. .......... 424/283

OTHER PUBLICATIONS

Alertsen, "ACTA Chem. Scand.," 9 (1955), No. 10, pp. 1725–1726.
Kasturi et al, "Tetrahedron Letters," No. 27 (1962) pp. 2573–2575.

Primary Examiner—Leonard Schenkman
Attorney, Agent, or Firm—Kenyon & Kenyon

[57] ABSTRACT

Potential insect control compounds which are chromenes, as well as their method of preparation and use, are disclosed. Compounds have been found which are effective in the control of insects by inhibiting the actions of juvenile hormone. Examples of useful compounds are 6,7-dimethoxy-2,2-dimethyl-3-chromene and 7-methoxy-2,2-dimethyl-3-chromene which can be extracted from the common bedding plant *Ageratum houstonianum*. Such compounds act to induce precocious maturation of immature insects, resulting in death either during or within a short time before or after the molting process. Additional effects which have been obtained include sterilization of mature insects, interruption of embryogenesis in insect eggs, the induction of diapause in insects and the prevention of sex pheromone secretion in insects.

13 Claims, No Drawings

ANTI-JUVENILE HORMONES

RELATED APPLICATION

This application is a continuation-in-part of Ser. No. 613,991, filed Sept. 17, 1975, now abandoned.

BACKGROUND AND SUMMARY OF THE INVENTION

The present invention is directed to compounds potentially useful in controlling insects. More particularly, the present invention is directed to active chromene compounds which are effective in inhibiting the effects of juvenile hormone in insects.

Of the various chemical compounds which have been employed in the prior art as insecticides for controlling insects, many of such prior art compounds have also been found to be harmful to humans and other animal life. In addition, many species of insect pests have developed a resistance and even immunity to available insecticides.

Alternative prior art methods for controlling insects have included the use of hormones, which interfere with the development of insects. Although such hormones have the advantage of apparently being harmless to other animals, their use is generally limited to application relatively late in the insect life cycle, after the insect has already produced its undesirable pest effect.

The endocrine systems of insects secrete a certain hormone known as juvenile hormone which functions to control the biological activities of metamorphosis, reproduction, diapause and sex attractant production. In particular, juvenile hormone functions initially to maintain the young developing insect in an immature condition until it has developed to the point where it is ready to molt to the adult form. When maturation of the insect begins, the body ceases to secrete juvenile hormone until after the insect has passed into the adult form, at which time secretion of juvenile hormone recommences in order to promote the development of the sex organs.

The forms in which juvenile hormone are known to occur in nature are discussed in the following publications: Trautmann et al., *Z. Naturforsch,* 29C 161-168 (1974); Judy et al., *Proc. Nat. Acad. Sci. USA,* 70, 1509-1513 (1973); Roller et al., *Angew. Chem. Int. Ed. Eng.,* 6, 179-180 (1967); Meyer et al., *Proc. Nat. Acad. Sci. USA,* 60, 853-860 (1968); Judy et al., *Life Sci.,* 13, 1511-1516 (1973); Jennings et al., *Life Sci.,* 16, 1033-1040 (1975); and Judy et al., *Life Sci.,* 16, 1059-1066 (1975).

In accordance with the present invention, it has been discovered that the lipid extract of the common bedding plant, Ageratum, contains two active compounds: (1) 6,7-dimethoxy-2,2-dimethyl-3-chromene; and (2) 7-methoxy-2,2-dimethyl-3-chromene; each of which is effective to inhibit the effects of juvenile hormone in insects. Both compounds have been described in the literature: A. R. Alertsen "Ageratochromene, a Heterocyclic Compound from the Essential Oils of some Agertaum Species", Acta Chem. Scand. 9 (1955) No. 10, pp. 1725-1726; R. Huls "Syntheses De Chromenes Substitutes", Bull. Soc. Chim. Belg., 67 (1958), pp. 22-32; R. Livingston et al., J. Chem. Soc., p. 1509 et seq. (1957); and T. R. Kasturi et al., Tetrahedron Lett. 27 (1967), p. 2573 et seq.

These and related chromene compounds inhibit the effects of Juvenile hormone, during early development of the insect and after reaching adulthood when the sex organs are undergoing development. By so inhibiting the effects of juvenile hormone, the maturing insect which has been treated with the present compounds is caused to die within a short time of such treatment. In addition, the ability of a treated insect to reproduce is prevented. The compounds of the present invention have also been found to interrupt embryogenesis in insect eggs, to induce diapause in insects and to prevent sex pheromone secretion in insects. The present compounds may be applied by suitable means including topically, orally or in a vapor state as a fumigant.

DETAILED DESCRIPTION OF THE PREFERRED EMBODIMENTS

Based upon the activity of the extracts of Ageratum, compounds potentially suitable for use as anti-juvenile hormones are selected from those with the following general structure of Formula I.

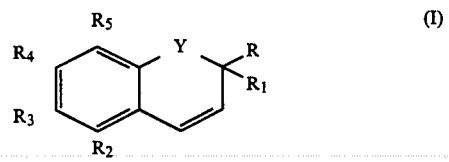

wherein:

R and $R_1$ are H, lower alkyl, straight or branched chain, of about 1 to 4 carbon atoms, lower alkoxy, straight or branched chain, of about 1 to 3 carbon atoms, Cl, Br or F;

$R_2$, $R_3$, $R_4$ and $R_5$ are H, lower alkyl, straight or branched chain, of 1 to 6 carbon atoms, lower alkoxy, straight or branched chain, of 1 to 6 carbon atoms, OH, $-OCH_2OCH_3$, $-OC_2H_4OC_2H_5$, $-CO-OCH_3$, $-CO-OCH_2CH_3$,

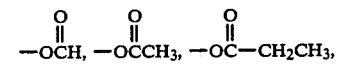

Cl, Br, F, $-SCH_3$, $-SCH_2CH_3$, $-SCH_2CH_2CH_3$, $-NO_2$, or the structure wherein $R_2$ and $R_3$, or $R_3$ and $R_4$, or $R_4$ and $R_5$ are joined with a $-OCH_2O-$ (methylenedioxy) group; or $-OCH_2CH_2-$(ethylenedioxy) group and Y is O, S or NH.

The present invention also relates to a process for the manufacture of compounds of the above formula, which process comprises reacting a compound of the general Formula II:

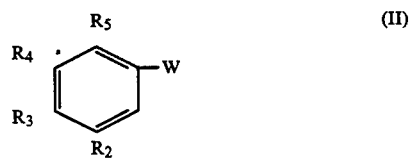

wherein W is OH, SH or $NH_2$ and $R_2$, $R_3$, $R_4$ and $R_5$ are substituents given in FIG. I, with a compound of the general Formula III:

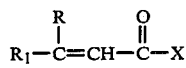

wherein, in Formula III:

X is H, OH, Cl, Br or I; and

R and $R_1$ are as given in connection with Formula I; in the presence of a Friedel-Crafts catalyst such as formic acid, $AlCl_3$, $ZnCl_2$, polyphosphoric acid, $SnCl_4$ or other similar catalyst well known in the art. A suitable solvent which is compatible with the Friedel-Crafts catalyst may be employed as necessary. Such a solvent may be, for example, ether, nitrobenzene or carbon disulfide. The reaction produces a chromanone of the general Formula IV:

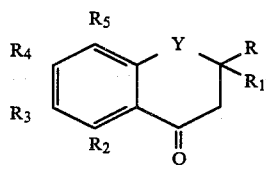

wherein the substituents are those given with regard to Formula I. The addition of heat, by means such as conducting the reaction on a steam bath for one to several hours, may be employed although such heating is not always necessary for obtaining the chromanone product.

The compounds of Formula IV are reduced with a reducing agent which may be any of those well known to one skilled in the art, such as lithium aluminum hydride or sodium borohydride, in a suitable solvent such as tetrahydrofuran or ether, to give a chromanol of the general Formula V:

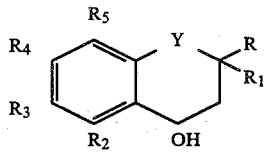

wherein the substituents are those given in connection with Formula I. If, following reduction, the reaction mixture containing the compounds of Formula V are treated with a dilute acid such as hydrochloric, toluenesulfonic or other similar acid well known to those skilled in the art, dehydration of the hydroxyl group occurs giving the chromenes directly corresponding to the compounds given in connection with Formula I. When the chromanols are isolated directly, subsequent treatment with a catalytic amount of acid such as toluenesulfonic in refluxing benzene causes dehydration to the chromene.

In the case of the reaction of the compounds of general Formula II with unsaturated aldehydes of Formula III in the presence of Friedel-Crafts catalysts, the desired chromenes are produced directly.

In alternative procedures, a compound having the structure of Formula II is reacted with one of the following:

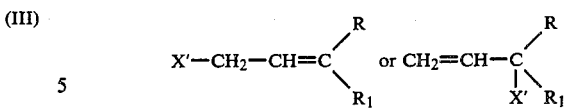

where R and $R_1$ have the meaning specified above and X' is a halogen or hydroxyl group. The chroman resulting from this reaction is then dehydrogenated by conventional techniques to give the corresponding chromene.

Preliminary screening of the compounds in addition to the Ageratum extracts indicates that the nucleus:

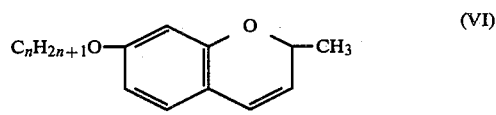

where n is from about 1 to 6, is important for activity. The nucleus may be modified in accordance with well known principles of molecular manipulation to produce compounds for screening. In particular the path followed for the synthesis of juvenile hormones and their analogs and homologs combined with the known techniques for producing insecticides suggests a useful approach to molecular modification.

A preferred method of this invention comprises contacting an insect with an anti-juvenile hormone selected from active compounds having the structure:

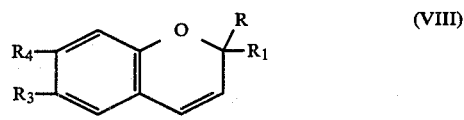

wherein R is methyl, $R_1$ is methyl or ethyl, $R_3$ is methoxy, ethoxy or H and $R_4$ is methoxy, ethoxy or propoxy, in an amount and concentration sufficient to alter the development of said insect. Alternatively $R_4$ may be methoxymethoxy or ethoxyethoxy.

A further embodiment of this invention comprises contacting an insect with an anti-juvenile hormone selected from active compounds which are dipyran benzenes having the substituents referred to above. In particular, the 1,7 and 1,9 dipyran benzenes, such as the following compounds, are useful: 6-methoxy-2,2,8,8,tetramethyl-1,7-dipyran benzene

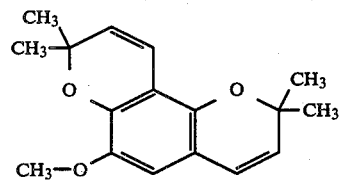

2,2,8,8-tetramethyl-1,7-dipyran benzene

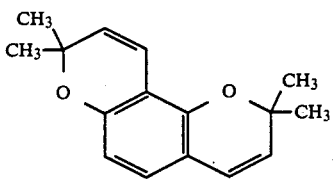

2,2,8,8-tetramethyl-1,9-dipyran benzene

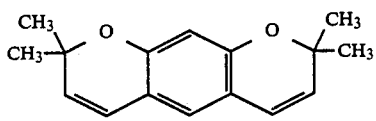

The following specific examples further illustrate the preparation of compounds within the scope of the general structures shown above.

EXAMPLE 1

Synthesis of 6,7-dimethoxy-2,2-dimethyl-3-chromene

The amount of 10 g of 3,4-dimethoxyphenol and 7.8 g of 3,3-dimethyl acrylic acid were combined in a 125 ml. erlenmeyer flask and dissolved with the addition of 40 ml anhydrous ethyl ether. The ether was removed in vacuo and while the contents of the flask remained liquid, 50 gm of polyphosphoric acid was added. The flask and contents were placed on a steam bath and heated with stirring for 1 hour. At the end of 1 hour, 75 ml. of water was added and the contents stirred into solution for 5 minutes. The solution was allowed to cool and a substantial sticky precipitate formed. The aqueous layer was decanted and extracted with 100 ml. of ether. The ether extract was washed successively with 150 ml. of water, 100 ml. of 5% sodium carbonate and 100 ml. of saturated NaCl solution. The ether extract was dried over anhydrous sodium sulfate. The sticky residue formed on cooling was dissolved in 300 ml. of chloroform and washed successively with 150 ml. of water, two 150 ml. portions of 5% sodium carbonate solution and 150 ml. of saturated NaCl solution. The chloroform solution was dried over anhydrous sodium sulfate. The ethereal and chloroform extracts were combined and the solvents removed in vacuo leaving 16.17 gm of off-white crystalline chromanone.

The chromanone was dissolved in 400 ml. of dry ethyl ether, and 2.5 gm of lithium aluminum hydride was added in portions. The reaction was refluxed for 2 hours and then allowed to come to room temperature. The excess lithium aluminum hydride was destroyed by dropwise addition of water and 150 ml. of 4N HCl was added slowly to the reaction mixture. Stirring was continued for 15 minutes. The reaction mixture was extracted with ether and washed successively with 100 ml. of water, 100 ml. 5% sodium carbonate solution and 100 ml. saturated NaCl solution. The ethereal extract was dried over anhydrous sodium sulfate. Removal of the ether in vacuo gave 15.6 g of crude chromene.

Distillation at 4 mm gave 10 gm of pure 6,7-dimethoxy-2,2-dimethyl-3-chromene BP 142°–144° C. The residue remaining after distillation was chromatographed over Florisil, trade name of a magnesium silicate adsorbent, and eluted with increasing concentrations of ether in petroleum ether to yield 2.2 g of additional pure chromene. The combined yield was 12.2 gm or a total yield of 79% of the theoretical. Purity was determined to be greater than 99% by thin-layer and gas-liquid chromatography. The structure was verified by infra-red and nuclear magnetic resonance spectroscopy.

An alternate synthesis involves the reaction of an appropriate phenol with 3-methyl-2-butene-1-ol or 3-methyl-1-bromo-2-butene or 3-methyl-1-butene-3-ol in the presence of a catalyst such as formic, 85% polyphosphoric acid, acetic acid or $ZnCl_2$ to produce the corresponding chromane. The chromane is treated with a dehydrogenating agent such as chloranil or DDQ (2,3-dichloro-5,6-dicyano-1,4-benzoquinone) in a suitable solvent such as benzene or xylene to introduce the double bond and give the corresponding chromene.

EXAMPLE 2

Synthesis of 6,7-methylenedioxy-2,2-dimethyl chromene 5.1 gm of 3-methyl-1-bromo-2-butene was combined with 4 gm of 3,4-methylenedioxyphenol and dissolved in 50 ml. of pentane and 50 ml. benzene. 2 gm of anhydrous $ZnCl_2$ was added and the reaction mixture refluxed for 1 hour and cooled. The mixture was extracted with ether and washed successively with 100 ml. of water, 100 ml. 5% sodium carbonate and 100 ml. of saturated salt solution. After drying the extract over anhydrous sodium sulfate, the solvent was removed in vacuo leaving 7.4 g of crude chromane. The crude material was fractionated on a column of Florisil and eluted with increasing concentrations of ether in petroleum ether to yield 4.5 g of pure chromane.

One gram of the chromane was dissolved in 75 ml. of benzene and 1.2 g of DDQ added. The reaction mixture was refluxed for 4 hours, then cooled and filtered. Removal of the solvent from the filtrate gave 1.35 g of crude product. Chromatography over Florisil gave 0.95 gm of pure 6,7-methylenedioxy-2,2-dimethyl-3-chromene. Structure and purity were determined by thin-layer and gas-liquid chromatography and NMR spectroscopy.

EXAMPLE 3

Synthesis of 6,7-dimethoxy-2-methyl-2-ethyl chromene

A complementary synthesis similar to the above involves reaction of an appropriate phenol with an allylic alcohol in the presence of formic acid to yield the chromane in high yield. This followed by dehydrogenation with chloronil or DDQ, gives the desired chromene.

Thus, 2 g of 3,4-dimethoxy phenol and 1.9 g of 3-methyl-1-pentene-3-ol were combined in 10 ml. formic acid with stirring at room temperature for 18 hours. Formic acid was removed in vacuo. The residue dissolved in ether was washed successively with 100 ml. of water, 100 ml. 5% sodium carbonate and 100 ml. saturated salt solution. The ether solution was dried over anhydrous sodium sulfate and gave 3.5 gm of crude product on removal of the ether in vacuo. Chromatography over Florisil gave 2.5 g of pure chromane. The amount of 0.88 gm of the pure chromane was dissolved in 100 ml. benzene and refluxed for 1 hour with 0.95 g DDQ. After cooling, filtration, and removal of the solvent, the filtrate gave 1.1 g crude product which on chromatography over Florisil gave 0.55 g of pure 6,7-dimethoxy-2-methyl-2-ethyl chromene. Purity and structure were determined by thin-layer and gas-liquid chromatography and by NRM spectroscopy.

EXAMPLE 4

Synthesis of 6,7-dimethoxy chromene

The synthesis of chromenes which are unsubstituted in the 2-position was accomplished by reaction of the appropriate phenol with acrylonitrile under basic catalysis to give the phenoxy-propionitrile which was converted to the corresponding phenoxy-propionate by treatment with acid. Ring closure to the chromanone was effected by treatment with polyphosphoric acid and the chromene obtained by reduction of the chromanone with any of several reagents such as lithium aluminum hydride or sodium borohydride followed by treatment with acid to promote dehydration to the chromene.

Thus 5 gm of 3,4-dimethoxyphenol; 6.88 g acrylonitrile and 0.5 ml. of Triton B, trade name of N-Benzyltrimethylammonium hydroxide, (40% soln.), were combined and refluxed for 18 hours. After cooling the reaction mixture was extracted with chloroform and washed with 5% sodium hydroxide, and with saturated salt solution. The organic layer after drying over anhydrous sodium sulfate gave 4.4 gm of 3,4-dimethoxy phenoxy propionitrile on removal of the solvent. The amount of 2.2 g of the nitrile was combined with 40 ml. of water and 80 ml. of concentrated hydrochloric acid and refluxed for 2 hours. The reaction mixture on cooling was extracted with ether and washed with water and 5% sodium hydroxide. The basic wash was acidified with 6N hydrochloric acid and extracted twice with ether. The ethereal extract was washed twice with water and with saturated salt solution. Drying over anhydrous sodium sulfate and removal of the solvent in vacuo gave 1.25 g of the crude 3,4-dimethoxy phenoxy propionic acid. The crude product was combined with 5 gm of polyphosphoric acid and heated at 75°–85° C. for 1 hour. The reaction mixture was extracted with ether and washed with 10% sodium carbonate solution and saturated salt solution. Drying over anhydrous sodium carbonate and removal of the solvent gave 0.35 gm of pure 6,7-dimethoxy chromanone. The chromanone was dissolved in 50 ml. dry ether and refluxed 1 hour with an excess of lithium aluminum hydride. On cooling, the reaction was stopped by addition of 10 ml. of water and then stirred for 15 minutes with 10 ml. of 2N hydrochloric acid. The reaction mixture was extracted with ether and washed with water and saturated salt solution to give on drying and removal of the solvent 0.31 gm of pure 6,7-dimethoxy chromene.

EXAMPLE 5

The following Table I provides a flow chart showing the isolation of the two natural products from Ageratum, including the column fractionation and thin-layer chromatography.

TABLE I

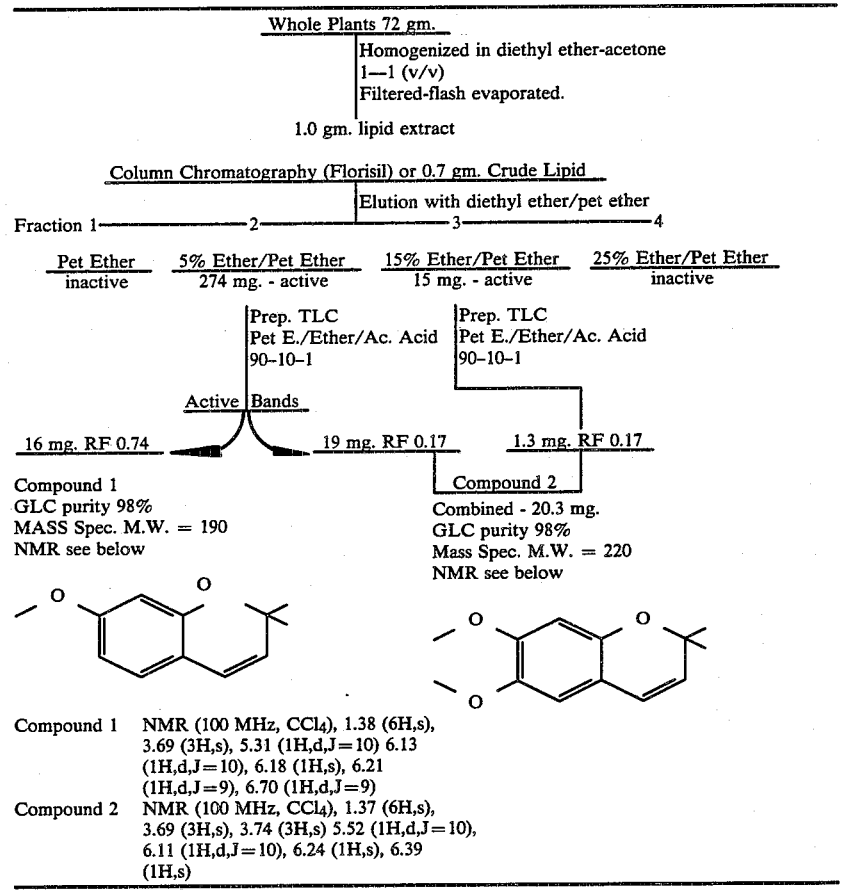

AGERATUM HOUSTONIANUM

Whole Plants 72 gm.
Homogenized in diethyl ether-acetone 1—1 (v/v)
Filtered-flash evaporated.

1.0 gm. lipid extract

Column Chromatography (Florisil) or 0.7 gm. Crude Lipid
Elution with diethyl ether/pet ether Fraction 1 — 2 — 3 — 4

| Pet Ether | 5% Ether/Pet Ether | 15% Ether/Pet Ether | 25% Ether/Pet Ether |
| inactive | 274 mg. - active | 15 mg. - active | inactive |

Prep. TLC Pet E./Ether/Ac. Acid 90–10–1

16 mg. RF 0.74 — 19 mg. RF 0.17 — 1.3 mg. RF 0.17

Compound 1
GLC purity 98%
MASS Spec. M.W. = 190
NMR see below

Compound 2
Combined - 20.3 mg.
GLC purity 98%
Mass Spec. M.W. = 220
NMR see below Compound 1  NMR (100 MHz, CCl$_4$), 1.38 (6H,s), 3.69 (3H,s), 5.31 (1H,d,J=10) 6.13 (1H,d,J=10), 6.18 (1H,s), 6.21 (1H,d,J=9), 6.70 (1H,d,J=9)

Compound 2  NMR (100 MHz, CCl$_4$), 1.37 (6H,s), 3.69 (3H,s), 3.74 (3H,s) 5.52 (1H,d,J=10), 6.11 (1H,d,J=10), 6.24 (1H,s), 6.39 (1H,s)

INDUCTION OF PRECOCIOUS DEVELOPMENT

In accordance with the present invention, active chromenes were found to cause precocious maturation when applied to an immature insect. The juvenile hormone (JH) is a natural insect hormone which acts to keep the developing insect immature until it is ready to molt to the adult form. When maturation of the insect begins, the insect ceases to produce JH and the insect matures to the adult form. The compounds of the present invention have been found to stop the action of JH and cause the immature insect to begin the maturation process. For some insects the induced lack of JH causes such rapid maturation that the immature insect dies shortly prior to, or during the molting process. In other insects the lack of JH causes them to molt into miniature adults which completely avoids the tremendous feeding potential of the immature stages and results in tiny adults which are sterile, very fragile and which die soon after molting. The anti-juvenile hormone action can be overcome by the application of exogenous juvenile hormone, which indicates that the anti-juvenile hormone compounds act by interfering with the synthesis of juvenile hormones.

Tables II and III illustrate the induction of precocious maturation by contacting the milkweed bug with a chromene in accordance with the present invention. Other Hemiptera are also quite sensitive, and precocious metamorphesis has been induced in Lygaeus kalmii Stal and in Dysdercus cingulatus. Satisfactory results have not been obtained in inducing precocious metamorphesis in Holometabola.

TABLE II

Induction of Precocious Maturation in the Milkweed Bug by Lipid Extract of Ageratum

| Crude Lipid Extract of Ageratum[1] Concentration μg/cm² | Precocious Adults %[2] |
|---|---|
| 15 | 100 |
| 7 | 80 |
| 4 | 27.8 |
| 2 | 0 |
| control | 0 |

[1]Ether-acetone (1-1) extract of macerated plant tissue.
[2]Twenty 2nd instar nymphs were continuously exposed to the extract residue spread over a 9 cm petri dish containing milkweed seeds and water. Insects molted to apparently normal 3rd and 4th instar nymphs and then molted precociously to adult insects.

At high concentrations a minor percentage of the treated nymphs are unable to molt and remain as nymphs until death.

TABLE III

Induction of Precocious Maturation in the Milkweed Bug by Pure Ageratochromene

| Ageratochromene[1] μg/cm² | Precocious Adults %[2] |
|---|---|
| 0.7 | 90 |
| 0.4 | 15 |
| control | 0.0 |

[1]Pure synthetic ageratochromene (6,7-dimethoxy-2,2-dimethyl-3-chromene). Twenty 2nd instar nymphs were confined in a 9 cm petri dish with the synthetic anti-JH compound prepared in accordance with the present invention.
[2]Insects molted to 3rd and 4th instars and then molted into precocious adults.

STERILIZATION

In the normal adult insect, JH (or gonadotropic hormone) is produced again after molting to the adult form and is then necessary for the development of the insect ovaries. Treatment of adult insects with 6,7-dimethoxy-2,2-dimethyl-3-chromene as described below in Table IV was found to prevent or stop the action of JH and the insect ovaries failed to develop. If the insect ovaries were developed at the time of treatment, they rapidly regressed to the undeveloped state. In either event, reproduction was prevented. This technique has been successful with insects in the orders Hemiptera, Diptera and Coleoptera.

TABLE IV

Sterilization of Insects With Anti-Juvenile Hormone

| Concentrations of synthetic Ageratochromene which prevented ovary development | Insect |
|---|---|
| 7.0 μg/cm²[1] | Adult Milkweed Bug (Oncopeltus fasciatus) |
| 7.0 μg/cm²[2] | Cotton Stainer (Dsydercus intermedius) |
| 1.5 μg/cm²[3] | Apple Maggot (Rhagoletis pomonella) |
| 1000 ppm spray[4] | Mexican Bean Beetle (Epilachna varivestis) |

[1]Eight newly emerged adults confined to treated 9 cm petri dish for 48 hours. Ovaries examined for development after 6 days.
[2]Ten newly emerged adults confined to treated 9 cm petri dish for 72 hours. Ovaries examined for development after 13 days.
[3]Forty-five newly merged apple maggot females were confined to a 9 cm petri dish containing a residue of the test compound for 30 hours. After treatment flies were held in oviposition cages and examined for ovarian development when control insects began oviposition.
[4]Ten newly emerged Mexican Bean Beetle females were sprayed while feeding on a bean plant with emulsified ageratochromene. Ovaries were dissected out and examined for development when controls began oviposition.

SEX PHEROMONE INHIBITION

The method of this invention is also useful to inhibit sex pheromone production. Pheromone producing virgin female cockroaches (Periplaneta americana L.) were treated topically with 6,7-dimethoxy-2,2-dimethyl-3-chromene in the manner used to induce diapause (see Table VII below). This leads to the termination of sex attractant secretion within five days whereas untreated control cockroaches continued to produce pheromone for at least fifteen days.

OVICIDAL ACTIVITY

The control of embryogenesis in the insect egg by juvenile hormone is poorly understood. However, molting is known to occur in certain insect eggs and juvenile hormones have been extracted from insect eggs, implying a presumptive role of JH during embryogenesis. As shown in Table V and VI below, 6,7-dimethoxy-2,2-dimethyl-3-chromene was found to demonstrate ovicidal activity by contact and by fumigation, presumably by interfering with JH production by the insect embryo.

TABLE V

Ovicidal Activity of Anti-Juvenile Hormone Compound by Contact Spray on Mexican Bean Beetle Eggs

| Concentration of Synthetic Ageratochromene in Spray[1] | % Hatch | % Dead Nymphs |
|---|---|---|
| 100 ppm | 2.7 | 100 |
| 10 ppm | 18.4 | 76.7 |
| control | 80.0 | 0.0 |

[1]Four day old eggs on bean leaves were sprayed with Ageratochromene in emulsion formulation.

TABLE VI

Ovicidal Activity of Anti-Juvenile
Hormone Compound by Fumigation

| Concentration (mg) Synthetic Ageratochromene Which Prevented Egg Hatch or Survival of 1st Instar Insects[1] | Insect |
|---|---|
| 0.5 mg | Milkweed Bug |
| 0.2 mg | Mexican Bean Beetle |

[1]Newly laid eggs were confined in watch glasses exposed to vapors of compound placed on lid of watch glass. A small percentage of nymphs or larvae sometimes emerged from the eggs but died within a few hours.

DIAPAUSE INDUCTION

Many insects enter a state known as diapause in order to survive inclement climatic conditions such as winter, hot dry summers, etc. During diapause insects do not feed, mate or reproduce. Diapause occurs in many insects when the production of JH ceases. As shown in Table VII below, 6,7-dimethoxy-2,2-dimethyl-3-chromene was found to stop the action of JH when applied topically and to cause the insect to go into diapause. Insects in diapause stop feeding, thus are enable to cause crop damage and if diapause is prolonged, the insects become weak and die. The induction of diapause with these anti-JH chemicals thus becomes a very unique method of insect control.

TABLE VII

Induction of Diapause in
Adult Colorado Potato Beetles

| Synthetic Ageratochromene Topical ($\mu$g)[1] | Insects Entering Diapause %[2] |
|---|---|
| 500 | 40 |
| 250 | 38 |
| 100 | 75 |
| control | 0 |

[1]Insects were treated topically on the abdomen with the anti-juvenile hormone in 1 $\mu$l of acetone and placed upon potato plants growing in soil.
[2]After 21 days insects remaining on the potato plants were judged non-diapausing. Insects which had entered the soil and become quiescent were screened from the soil and judged to be diapausing.

FURTHER SCREENING

Preliminary screening indicates that numerous chromenes having the formula or the nucleus:

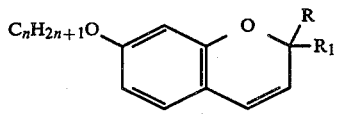

where R is methyl, $R_1$ is methyl or ethyl and n is 1 to 6, or preferably n is 1 to 3, induce precocious maturation. The tables below set forth numerous useful compounds against the milkweed bug and provide a basis for further molecular modification to produce chromenes for the present invention.

TABLE VIII

Induction of Precocious Maturation
and Sterilization of Milkweed Bug
by Anti-Juvenile Hormone Compounds

| Compound | Concentration ($\mu$g/cm$^2$)* (% Precocious Adults) |
|---|---|
| 6,7-dimethoxy-2,2-dimethyl-3-chromene | 1.9 (100%) |
| 6,7-diethoxy-2,2-dimethyl-3-chromene | 1.9 (100%) |
| 6-ethoxy-7-methoxy-2,2-dimethyl-3-chromene | 1.9 (100%) |
| 6-methoxy-7-ethoxy-2,2-dimethyl-3-chromene | .4 (100%) |
| 6-methoxy-7-isopropoxy-2,2-dimethyl-3-chromene | .8 (100%) |
| 6-methoxy-7-propoxy-2,2-dimethyl-3-chromene | 3.9 (100%) |
| 6-methoxy-7-butoxy-2,2-dimethyl-3-chromene | 3.9 (50%) |
| 6-methoxy-7-hexoxy-2,2-dimethyl-3-chromene | 3.9 (15%) |
| 6,7-dimethoxy-2-methyl-2-ethyl-3-chromene | 3.9 (50%) |
| 7-ethoxy-2,2-dimethyl-3-chromene | 3.9 (100%) |
| 7-methoxy-2,2-dimethyl-3-chromene | 3.9 (60%) |
| 6-bromo-7-ethoxy-2,2-dimethyl-3-chromene | 3.9 (15%) |

*In the standard procedure, twenty 2nd instar nymphs were confined to 9 cm petri dishes containing the anti-juvenile hormone. Precocious adults were examined after 5 days for ovarian development and were determined to be sterile.

Analogs of the foregoing compounds have also been found useful and are listed below.

TABLE IX

| Compound | Concentration ($\mu$g/cm$^2$) (% Precocious Adults) Milkweed Bug |
|---|---|
| 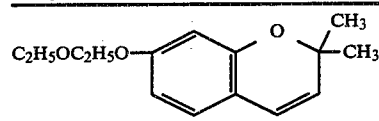<br>7-ethoxyethoxy-2,2-dimethyl-3-chromene | 3.9 (100%) |
| 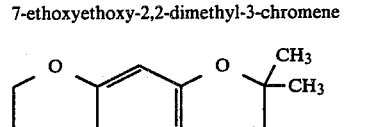<br>6,7-ethylenedioxy-2,2-dimethyl-3-chromene | 3.9 (limited activity) |
| 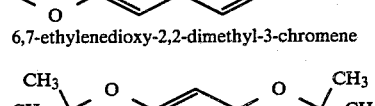<br>2,2,8,8-tetramethyl-1,9-dipyran benzene | 1.9 (20%) |
| 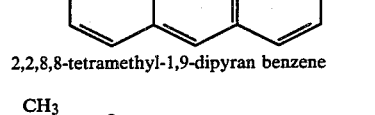<br>2,2,8,8-tetramethyl-1,7-dipyran benzene | 1.9 (45%) |
| 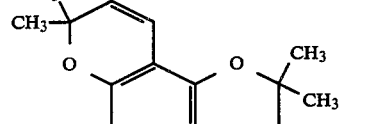<br>6-methoxy-2,2,8,8-tetramethyl-1,7-dipyran benzene | 1.9 (100%) |

Additional compounds have been preliminarily screened without satisfactory results in inducing precocious maturation in the milkweed bug but which have led to sterilization of the milkweed bug. These compounds are listed in Table X.

TABLE X 6,7-dimethoxy-3-chromene
6,7-dimethoxy-2-methyl-3-chromene
7-methoxy-6-hydroxy-2,2-dimethyl-3-chromene 7(3-propynyloxy)-2,2-dimethyl-3-chromene:

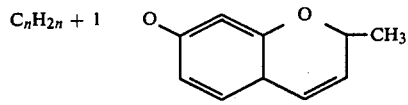

6,7-dimethoxy, 2,2-dimethyl-3,4-cycloprop-chroman:

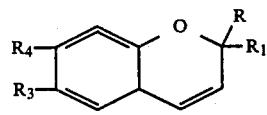

6,7-dimethoxy, 2,2-dimethyl-3,4-cycloprop (dichloro)-chroman:

The remaining chromenes and their analogs which have been preliminarily tested have not provided satisfactory results. Similarly unsuccessful preliminary results have been obtained on certain insects other than those reported above. These results are not sufficiently definitive to determine whether such compounds lack any utility and more comprehensive testing appears necessary against various types of insects. However, the broad new approach to insect control evidenced by the foregoing data provides an impetus and a basis for further screening of chromenes, their analogs, and the techniques of application to optimize this invention.

The screening procedure for determining anti-juvenile hormone activity is readily carried out by contacting an immature insect, preferably a 2nd instar nymph, with a compound to be tested in a concentration which can vary greatly. Either direct contact or contact with the insect's environment with from about 0.4 to 4 $\mu g/cm^2$ of the compound to be tested is a useful procedure. The insect is then observed to determine its mode of further development. A further screening technique is to test for sterilization, or other effects of anti-juvenile hormones, in the manner set forth in the above description and examples. By these techniques the potentially usefull compounds within the scope of Formula I and analogs of these compounds are readily screened to determine which are suited for different application conditions and insects.

This invention is further set forth in the publication "Discovery of Insect Anti-Juvenile Hormones in Plants" by Bowers et al., Science, Vol. 193, pp. 542–547 (Aug. 13, 1976), incorporated herein by reference.

What is claimed is:

1. A method of treating an insect to inhibit the juvenile hormone activity in said insect and thereby effect insect control which comprises contacting an insect with an active chromene compound which is an anti-juvenile hormone having the nucleus:

wherein n is an integer from about 1 to 6 in an amount effective to inhibit the effects of juvenile hormone.

2. The method of claim 1 wherein said active chromene compound is characterized in a screening test as inducing precocious maturation in an immature insect after contact with said insect in a concentration of about 0.4 to 4 micrograms per square centimeter.

3. The method of claim 2 wherein said insect is selected from the genus hemiptera.

4. A method of treating an insect to inhibit the juvenile hormone activity in said insect and thereby effect insect control which comprises contacting an insect with an active anti-juvenile hormone having the structure wherein R is methyl, $R_1$ is methyl or ethyl, $R_3$ is methoxy, ethoxy or H and $R_4$ is methoxy, ethoxy or propoxy in an amount and concentration sufficient to inhibit the effects of juvenile hormone.

5. The method of claim 4 wherein said active chromene compound is characterized in a screening test as inducing precocious maturation in an immature insect after contact with said insect in a concentration of about 0.4 to 4 micrograms per square centimeter.

6. The method of claim 5 wherein said insect is selected from the genus hemiptera.

7. The method of treating an insect to inhibit the juvenile hormone activity in said insect and thereby effect insect control which comprises contacting an insect with an active anti-juvenile hormone wherein said hormone is selected from the group consisting of 7-ethoxy-2,2-dimethyl-3-chromene; 6,7-diethoxy-2,2-dimethyl-3-chromene; 6-methoxy-7-isopropoxy-2,2-dimethyl-3-chromene; 6-methoxy-7-propoxy-2,2-dimethyl-3-chromene; 6-methoxy-7-butoxy-2,2-dimethyl-3-chromene; and 6,7-dimethoxy-2methyl-2-ethyl-3-chromene in an amount effective to inhibit the effects of juvenile hormone.

8. A method of treating an insect to inhibit the juvenile hormone activity in said insect and thereby effect insect control which comprises contacting an insect with an anti-juvenile hormone selected from the group consisting of:

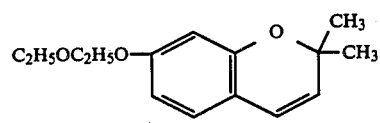

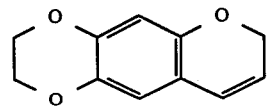

-continued

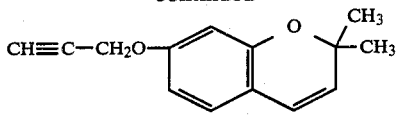

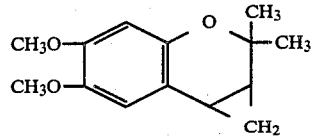

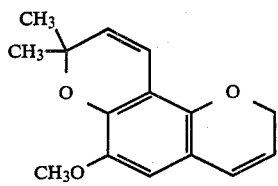

and

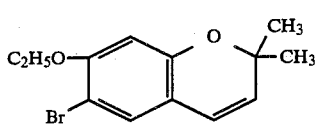

in an amount effective to inhibit the effects of juvenile hormone.

9. A method of treating an insect to inhibit the juvenile hormone activity in said insect and thereby effect insect control which comprises contacting said insect with an effective amount sufficient to inhibit the effects of juvenile hormone with a compound selected from the group consisting of 6,7-dimethoxy-2,2-dimethyl-3-chromene; 7-methoxy-2,2-dimethyl-3-chromene; 6-methoxy-7-ethoxyl-2,2-dimethyl-3-chromene; and 6-ethoxy-7-methoxy-2,2-dimethyl-3-chromene.

10. A method of controlling insects which comprises treating an immature insect with a sufficient amount of an anti-juvenile hormone which interferes with the production of juvenile hormone by the insect and causes precocious maturation wherein said anti-juvenile hormone is an active chromene compound which upon contact in effective amounts with an immature insect leads to the development of a sterile and short-lived adult insect.

11. The method of treating an insect to inhibit the juvenile hormone activity in said insect and thereby effect insect control which comprises contacting an insect with an active anti-juvenile hormone in an amount and concentration sufficient to inhibit the effects of juvenile hormone, said anti-juvenile hormone having the following structure:

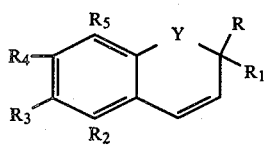

wherein:
R and $R_1$ are H, lower alkyl, straight or branched chain, of 1 to 4 carbon atoms, lower alkoxy, straight or branched chain, of 1 to 3 carbon atoms, Cl, Br or F;
$R_2$, $R_3$, $R_4$ and $R_5$ are H, lower alkyl, staight or branched chain, of 1 to 6 carbon atoms, lower alkoxy, straight or branched chain, of 1 to 6 carbon atoms, OH, $-OCH_2OCH_3$, $-OC_2H_4OC_2H_5$, $-CO-OCH_3$, $-CO-OCH_2CH_3$,

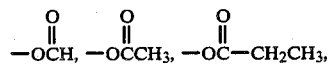

Cl, Br, F, $-SCH_3$, $-SCH_2CH_3$, $-SCH_2CH_2CH_3$, $-NO_2$, or the structure wherein $R_2$ and $R_3$, or $R_3$ and $R_4$, or $R_4$ and $R_5$ are joined with a $-OCH_2O-$ group; or $OCH_2CH_2-O-$ group and
Y is O, and
wherein said active compounds are characterized as those which upon contact with an immature insect in an effective amount will cause precocious maturation of the insect.

12. A method of controlling insects comprising applying to the insect or habitat thereof an effective controlling amount of the compound having the formula

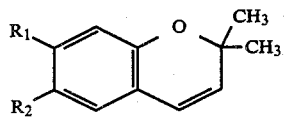

in which $R_1$ is 2-propynoxy and $R_2$ is hydrogen.

13. A compound having the formula

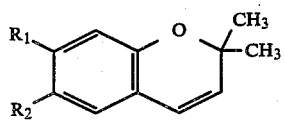

in which $R_1$ is 2-propynoxy and $R_2$ is hydrogen.

* * * * *